United States Patent
Desgrandchamps et al.

(10) Patent No.: US 6,296,668 B1
(45) Date of Patent: Oct. 2, 2001

(54) ARTIFICIAL IMPLANT INTENDED TO REPLACE THE HUMAN URINARY AND EXCRETORY ORGANS

(75) Inventors: Francois Desgrandchamps, Paris; Alain Le Duc, Neuilly sur Seine, both of (FR)

(73) Assignee: Assistance Publique-Hopitaux de Paris, Paris (FR)

( * ) Notice: Subject to any disclaimer, the term of this patent is extended or adjusted under 35 U.S.C. 154(b) by 0 days.

(21) Appl. No.: 09/350,056

(22) Filed: Jul. 8, 1999

Related U.S. Application Data

(63) Continuation of application No. PCT/FR98/00200, filed on Feb. 4, 1998.

(30) Foreign Application Priority Data

Feb. 14, 1997 (FR) .................................................. 97 01762

(51) Int. Cl.$^7$ .................................................. A61F 2/36
(52) U.S. Cl. .................................................. 623/23.65
(58) Field of Search ........................ 623/23.64, 23.65, 623/23.66, 23.67, 23.68

(56) References Cited

U.S. PATENT DOCUMENTS

| | | | | |
|---|---|---|---|---|
| 3,750,194 | * | 8/1973 | Summers | 623/23.64 |
| 3,953,897 | * | 5/1976 | Chevallet | 623/23.64 |
| 4,044,401 | * | 8/1977 | Guiset | 623/23.64 |
| 4,228,550 | * | 10/1980 | Salkind | 623/23.64 |
| 4,334,327 | * | 6/1982 | Lyman | 623/23.64 |
| 4,969,902 | * | 11/1990 | Ravo | 623/23.64 |
| 4,976,735 | * | 12/1990 | Griffith | 623/23.64 |
| 5,041,136 | * | 8/1991 | Wascher | 623/23.64 |
| 5,370,690 | * | 12/1994 | Barrett | 623/23.64 |
| 5,397,354 | * | 3/1995 | Wilk | 623/23.64 |
| 5,902,337 | * | 5/1999 | De Lelio | 623/23.64 |

FOREIGN PATENT DOCUMENTS

| | | |
|---|---|---|
| 372 311 | 6/1990 | (EP) . |
| 2 255 877 | 7/1975 | (FR) . |
| WO 93/16659 | 9/1993 | (WO) . |

OTHER PUBLICATIONS

"A Prosthetic Urinary Bladder—Why Not?"; *Mayo Clin. Proc.*; vol. 67, pp. 293–295; 1992.
D. Rohman et al.; "Alloplastic replacement of the Urinary bladder"; *J. of Urology*; vol. 156, pp. 2094–2097; 1996.
Copy of International Search Report for PCT/FR98/00200.

* cited by examiner

*Primary Examiner*—Michael Milano
(74) *Attorney, Agent, or Firm*—Merchant & Gould P.C.

(57) ABSTRACT

The object of the invention is an implant not requiring major surgery for its insertion or for the partial replacement of any of its elements; said prosthesis can be applied for long-term placement. The implant disclosed replaces the entire urinary organs, thereby precluding any possible anastomosis, said implant comprising a double-layered (7, 8) structure for the artificial replacing elements: tubular elements (1, 3) for the renal ducts and urethra, a reservoir (2) for the bladder, and an artificial urethral sphincter (4). The aritificial tubular elements of renal ducts (1) are connected to the reservoir (2) by mechanical attachments (5), said elements (1 to 3) being constituted and formed so that they can pass from a flattened state when empty to an expanded state. The two layers (7, 8) join to form the tubular elements (1, 3), forming respectively an external shell which is sufficiently flexible to submit to deformation by manual pressure, and an internal pocket, which is supple and extractable from the shell, constituting the reservoir (2). This structure allows for the partial replacement of each of its elements and ensures the long-term placement of the prosthesis.

11 Claims, 5 Drawing Sheets

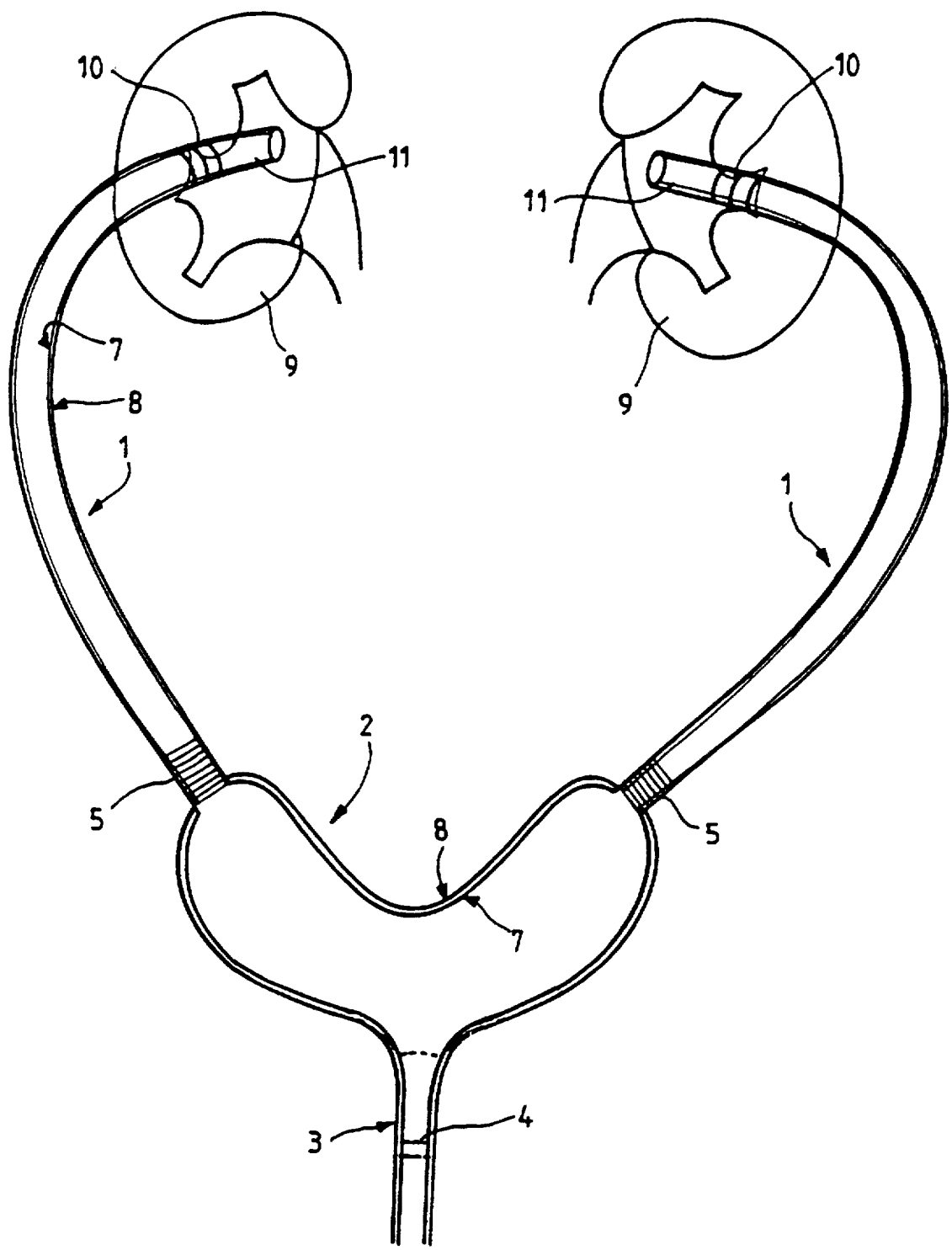
FIG_1

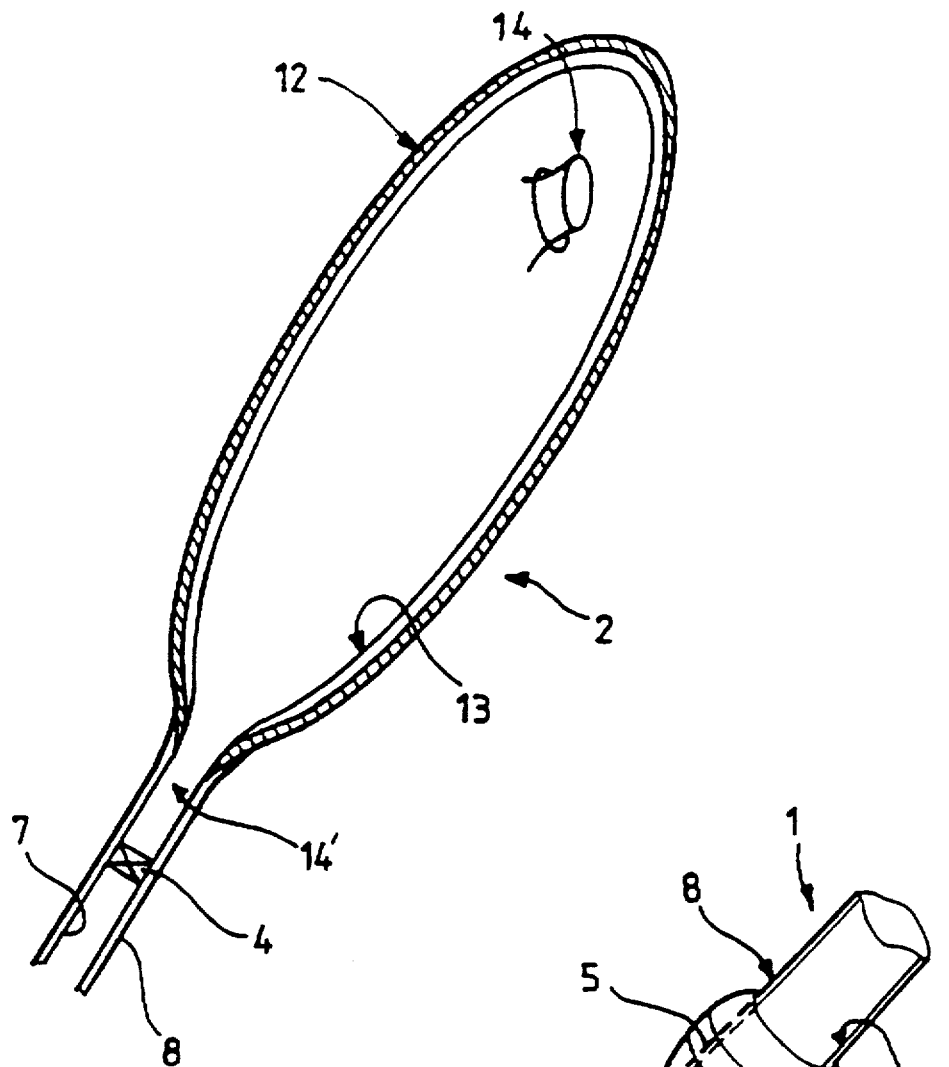
FIG_2
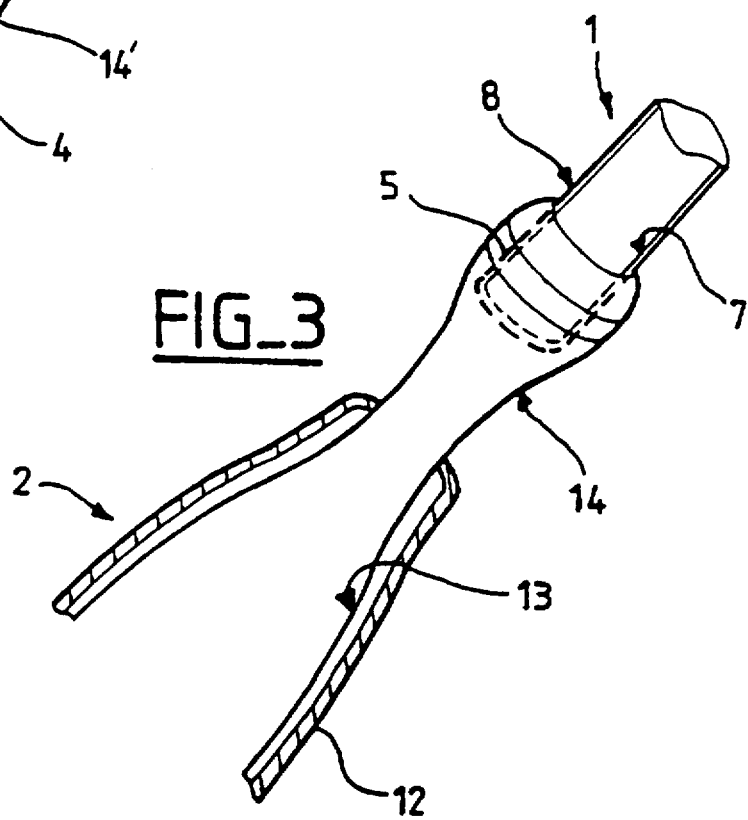
FIG_3

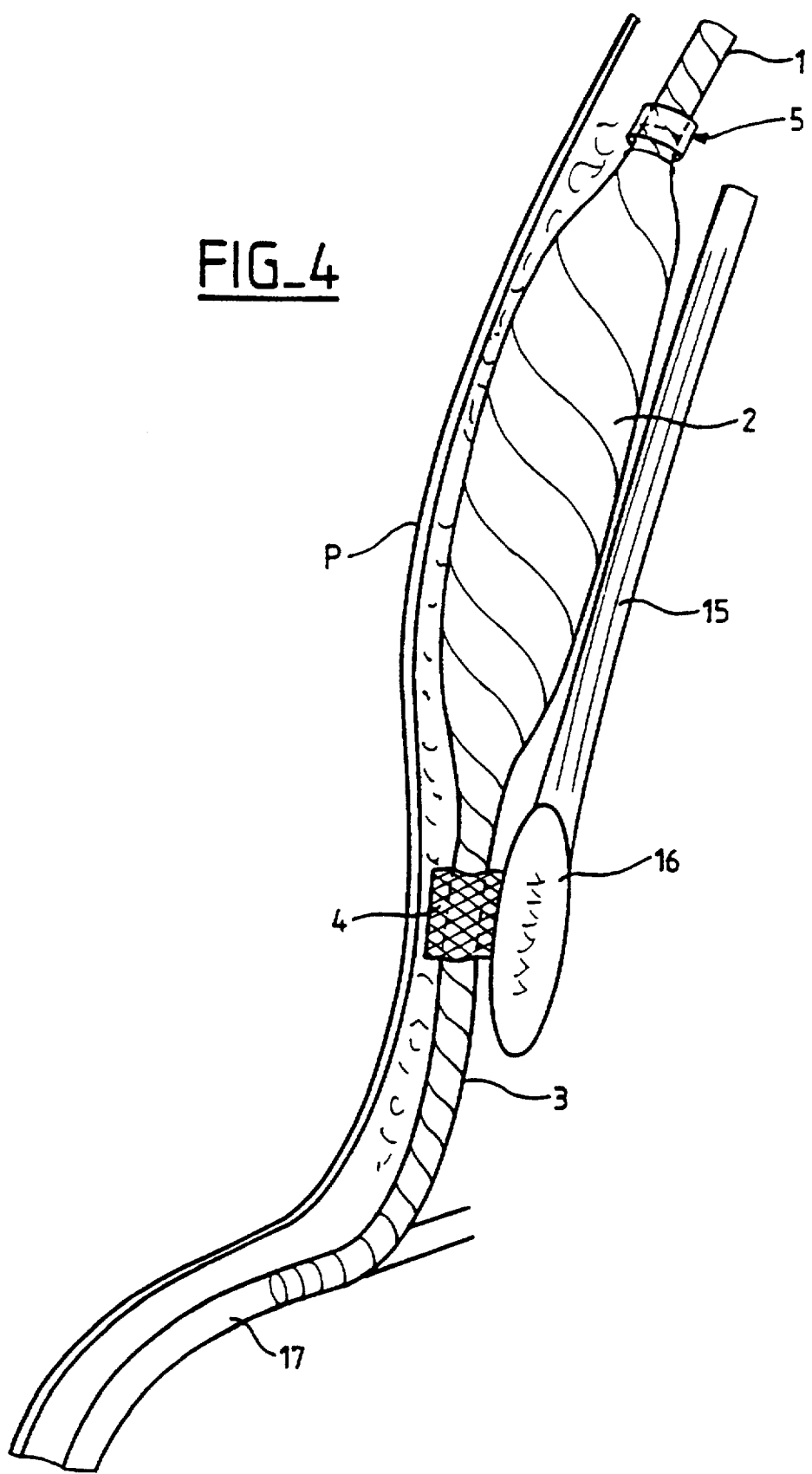
FIG_4

FIG_5
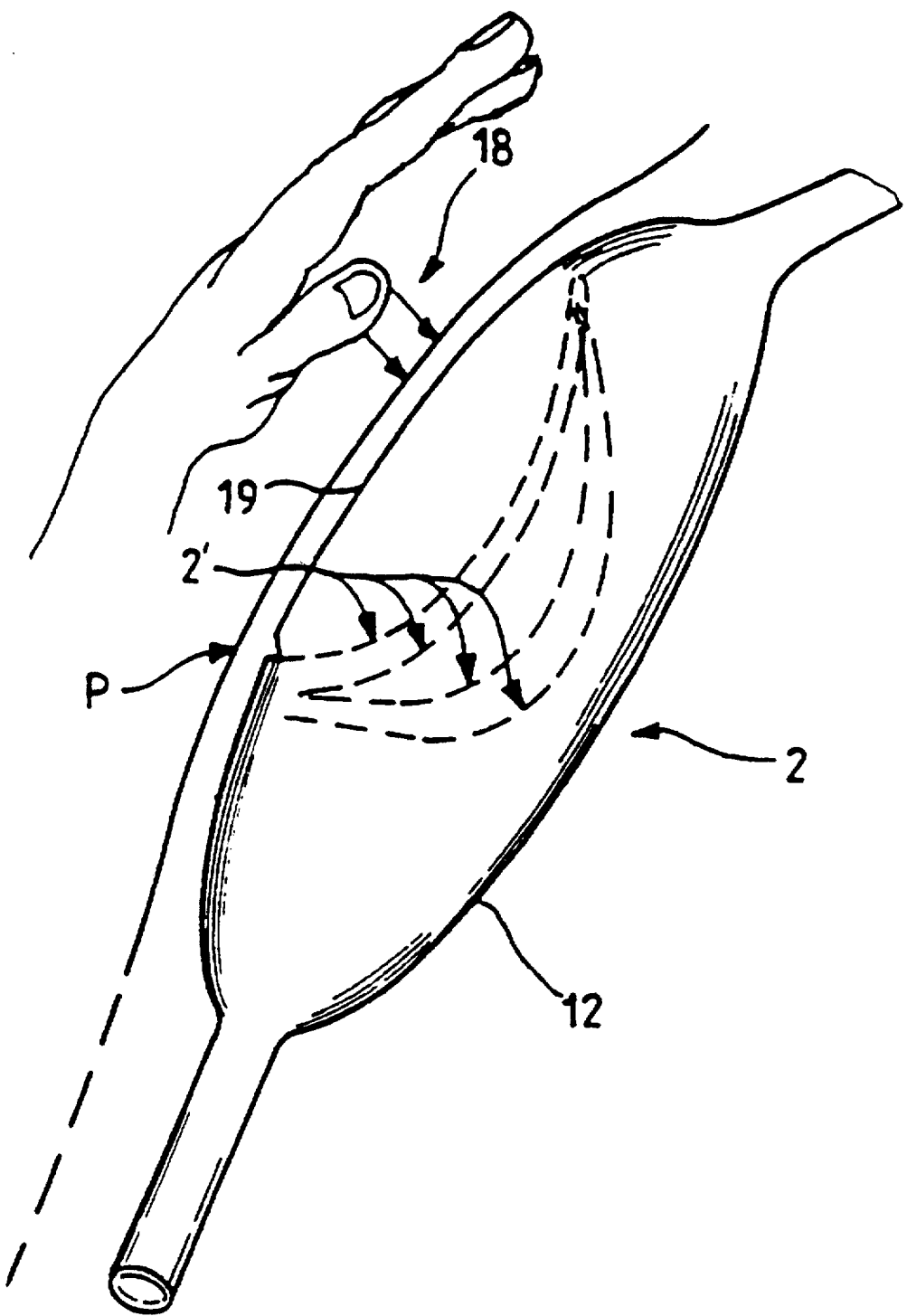

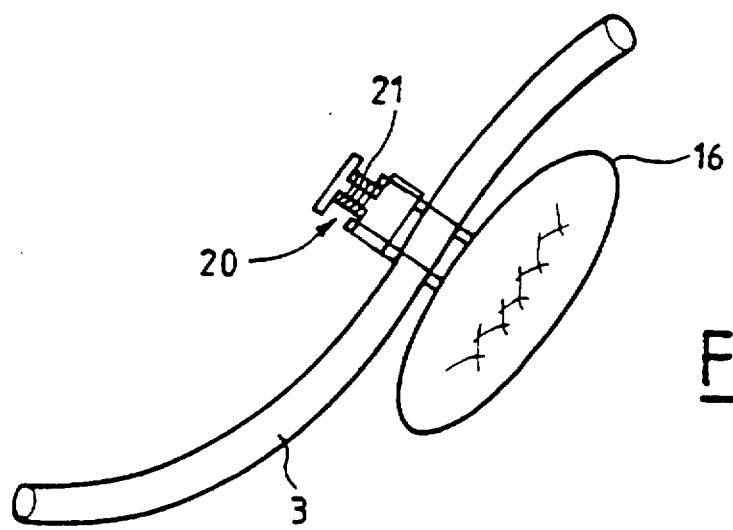
FIG_6a
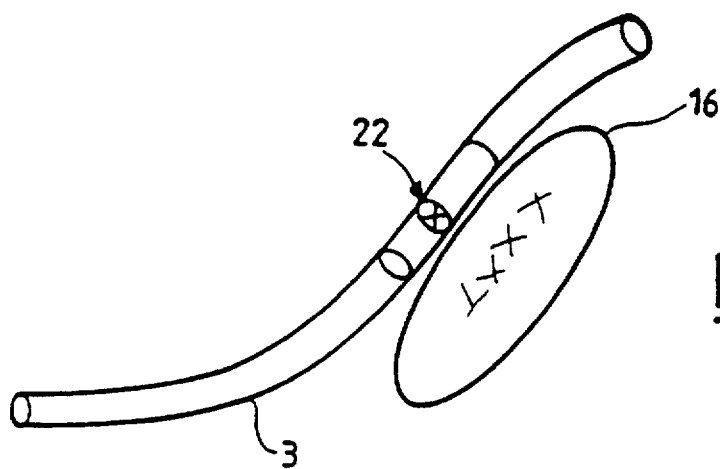
FIG_6b
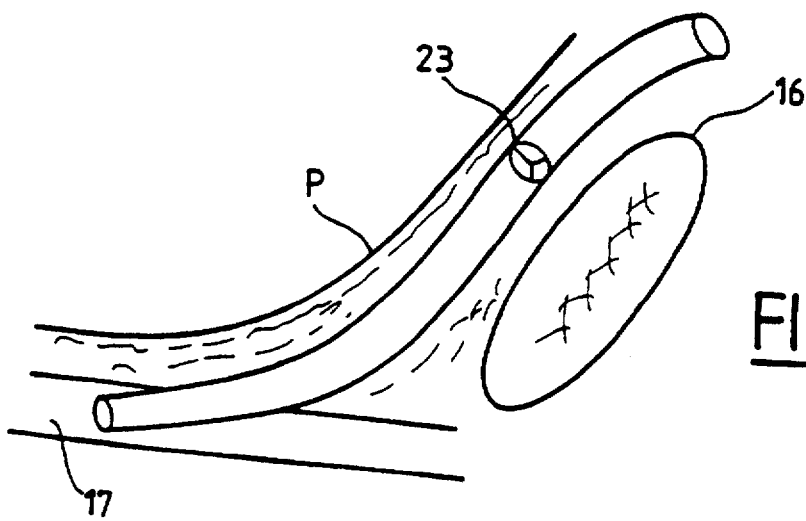
FIG_6c

ARTIFICIAL IMPLANT INTENDED TO REPLACE THE HUMAN URINARY AND EXCRETORY ORGANS

This application is a continuation of PCT/FR98/00200 filed Feb. 4, 1998.

BACKGROUND OF THE INVENTION

1. Field of the Invention

The present invention relates to artificial implants to replace the male and female human urinary and excretory organs.

One of the principal functions of the urinary and excretory organs is to collect and carry the fluids produced by renal metabolism via the urethras towards the bladder, where those liquids can be stored for a short period. When the liquids reach a certain level and exert a certain pressure on the bladder walls, they are carried to the exit via the urethra, where the operation of a muscle, the sphincter, enables them to be evacuated by acting as a valve.

Replacement of all or a portion of the urinary and excretory organs is indicated, for example, in patients who have undergone a total cystectomy due to cancer of the bladder or a pelvic resection as a result of rectal or cervical cancer. Other indications for this type of replacement are vesicle neurological attacks or interstitial cystitis, tuberculosis, irradiation or schistosomiasis or certain congenital deformities.

2. Description of the Related Art

Only natural implants, using biological material constituted by a variety of organic tissues, essentially intestinal grafts, have until now been able to be used in man without medium term rejection.

However, such biological implants raise a number of problems as regards reflux of liquid, infections, mucous secretions, or as regards absorption of secreted urinary products and ostomal complications.

Such disadvantages have resulted in the development of artificial implants presenting fewer risks than natural biological implants.

A number of models for artificial bladders, ureters, urethras or sphincters comprising a plurality of materials have been separately and experimentally developed for animals but apart from an artificial sphincter, none have been successfully used for a long period of time in humans.

The development of prostheses causing fewer complications after implantation has thus been attempted. Materials tested include vitellium, Teflon®, polyvinyl, Ivalon®, Dacron®, silver, tantalum, as well as expanded polytetrafluoroethylene (Gore-Tex®).

The majority of materials used have not provided satisfactory results, either because of the rapid development of infections linked to bacterial adhesion to the materials employed, or to the formation of stones, deformation or detachment of the prosthesis, reflux of liquids towards the kidneys, or the rupture of elements of the implant at the anastomoses, the joins between artificial and natural elements.

An ideal material for such an artificial organ intended for implantation inside the human body is one which resists bacterial adhesion. It is also biocompatible so as to be tolerated well by the surrounding tissue and so as not to induce rejection reactions which cause inflammation.

Further, the artificial implant is preferably filled with a small increase in the intraluminal pressure, so as to retain its capacity to refill after emptying and so that it does not collapse.

An additional problem which has to be overcome by using an artificial implant intended to replace portions of the urinary and excretory organs is the reduction in the service life of the implant in situ. This problem is essentially due to fluid leakage (urine being highly corrosive in nature) around the anastomosed connections between the different elements, to the cicatrization of tissue around the prosthesis and more particularly to deposition of detritus contained in urine on the various elements of the prostheses which lead to their deterioration or even obstruction.

One cause of failure as regards the duration of the emplacement of artificial implants results from the use of the materials used above which necessitate periodical replacement of the implanted prosthesis by major surgical intervention, such surgery requiring the anastomoses formed to be destroyed to allow withdrawal.

Silicone gum is known to prevent encrustation of bacteria and constitutes a suitable material for artificial implants which have to come into contact with body fluids over a long period.

However, when artificial silicone bladders were implanted in the abdominal cavity of dogs, with Teflon® connectors comprising Marlex® mesh to provide a fibrous function, fluid tight anastomoses were obtained but intestinal complications following rejection due to intolerance of the organism to silicone developed as a result.

An artificial implant intended to replace the bladder should cause neither rejection as a foreign body nor infection nor incrustation nor liquid reflux, nor dilation of higher tracts. Currently, partial replacement of the elements of the urinary system has been disclosed, but the devices used are complex and require sophisticated hydraulic pumping means to control the down-flow of urine and to control bladder emptying.

In this regard, U.S. Pat. No. 5,370,690 by David M Barret discloses an artificial bladder constituted by a rigid outer shell of polysulphone and a flexible inner silicone reservoir. Those two elements delimit between them an open space which can be filled with a biocompatible fluid to a predetermined pressure. The intermediate space is connected to a reservoir and to pumping means which, by exerting pressure, enable the inner reservoir containing urine to be emptied. The device also comprises ureters carrying non-return valves to prevent urine from rising from the bladder towards the kidneys.

The publication "Alloplastic replacement of the urinary bladder" by D. Rohrman et al., in J. of Urology, vol. 156, pages 2094–2097 (1996), describes the replacement of the entire urinary system by a unit constituted by two lateral reservoirs implanted subcutaneously. Problems with fluid reflux from the reservoirs constituting the bladder towards the kidneys subsist, necessitating the installation of two non-return valves in the two catheters connecting the reservoirs to the kidneys.

French patent FR-A-2 255 877 by J. Chevallet and A. Sausse describes a vesical prosthesis which is implantable in the intra-abdominal cavity, which can be connected to ureters and to the urethra of a patient or to prosthetic ureters and/or urethra, which has no artificial valves or flaps, enabling the patient to manually control it.

The device disclosed in that patent comprises a reservoir constituted by a flexible plastics material, preferably a vulcanised elastomer, which gives it the property of returning to its original form after having been deformed by urine being emptied. That device also envisages replacement of the conduits for uretral connections and/or evacuation of urine through the abdominal or perineal wall. Those connections with the remaining natural elements are effected via sleeves of colonisable textile material aimed at encouraging anastomosis to ensure that the implant is held in place.

That device is intended to occupy the position of the natural bladder such that the abdominal muscles contribute to emptying it by exerting a limited pressure. Thus major surgery is required to insert the implant and replace the natural bladder.

In addition to Barret's artificial implant, D. P. Griffith describes a variety of devices in the publication "A prosthetic urinary bladder why not?" in Mayo Clin. Proc. Vol. 67, pp. 293–295, 1992 and emphasises the problems which are not solved by existing implants, namely inflammation caused by inserting artificial tubes into the ureters and/or urethra and liquid tightness problems which occur, in particular at the anastomoses.

SUMMARY OF THE INVENTION

The aim of the invention is to solve the problems described above and in particular to provide an implant which does not require major surgical intervention to insert it or for partial replacement of one of its elements, while enabling the prosthesis to remain in place for a long period. To this end, the implant of the present invention is an integral replacement of the urinary system to prevent the need for any anastomosis, and has a particular double layered structure for all of the organs of the urinary system. This structure permits partial replacement of each of its elements and ensures that the prosthesis can remain in place for a long

BRIEF DESCRIPTION OF THE DRAWINGS

FIG. 1 is a general sectional view of an artificial implant of the present invention.

FIG. 2 is a sectional view along the line II—II of the reservoir of the implant of FIG. 1, intended to replace the bladder.

FIG. 3 is a partially cut away view of a mechanical connection between the reservoir and an artificial ureter of the present invention.

FIG. 4 is a partial side view of the implant of the present invention.

FIG. 5 is a section representing the state of the reservoir during emptying.

FIGS. 6a to 6c are three examples of artificial urethral sphincters.

DESCRIPTION OF THE PREFERRED EMBODIMENTS

More precisely, the invention provides an artificial implant, of t integral replacement type, comprising as artificial elements to substitute the organs of the human urinary system, tubular elements for the ureter and urethra, a reservoir for the bladder, and an artificial urethral sphincter. The artificial elements are structured as a mixed double-layered arrangement and are connected together by mechanical connections. The composition and form of these elements are such as to permit their passage between a flattened state when empty and an expanded state. The two layers comprising the tubular elements are integral and the two layers comprising the reservoir respectively form an outer shell, which is sufficiently flexible to be deformable by manual pressure, and an inner pouch which is flexible and can be extracted from the shell.

The mixed structure of the invention is adapted to ensure liquid tightness of the anchorages to the kidneys and to eliminate the risks of developing infections and to eliminate rejection by surrounding tissue. The implant of the invention means that repeated surgical intervention can be avoided and thus the costs inherent in this type of intervention are reduced.

The inner layer remains in contact with the fluids and has a low capacity for adherence to residues, for example bacteria, proteins, crystals which are normally present in urine and which can become encrusted on the walls of the implant, and a high degree of flexibility so as to be extractable through a slot type aperture. The inner layer is, for example, composed of silicone gum.

The inner pouch of the reservoir can thus be readily extracted for replacement with a new pouch via incisions used in minor surgery, without intervention into the other elements of the implant.

In addition to its flexibility, the material of the outer layer of the double-layer structure advantageously has a high degree of biocompatibility. It is, for example, constituted by expanded polytetrafluoroethylene.

Preferably, manual means for direct pressure with a spring system, or mechanical or electromechanical means are implemented for emptying.

The different elements composing the artificial implant of the present invention are preferably connected together by mechanical connections. Advantageously, this type of connection solves the problems of liquid tightness of artificial implants in current use, and are limited to the replacement of one or other of the natural components of the urinary system.

The use of mechanical connections between the different components (ureters, bladder, urethra and sphincter) together with direct anchorage of the ureters in the kidneys holds the assembly together and dispenses with the formation of anastomoses.

Because of the materials used, implanting the urinary system of the invention into a superficial layer enables the bladder to be emptied and the urethral sphincter to be opened by simple manual pressure. Further, subcutaneous implantation instead of location in the normal abdominal location for this type of implant means that only non invasive surgical intervention, which can be carried out on a large number of patients, needs to be carried out.

The artificial implant of the present invention shown in FIG. 1 replaces the entire natural human urinary system, principally constituted by the bladder, the ureters, the urethra and the urethral sphincter.

The implant principally comprises a reservoir 2, intended to replace the bladder, to which tubular elements 1 are connected via mechanical connections 5, the tubular elements constituting artificial ureters for connection to the kidneys 9. Reservoir 2 extends into a tubular element 3 constituting the artificial urethra, comprising an artificial sphincter 4.

Each of elements 1 to 4 of the implant of the present invention is constituted by a mixed double-layered structure composed of an inner layer 7 and an outer layer 8 of different materials, respectively of silicone gum and expanded polytetrafluoroethylene.

The inner layer prevents biological residues (proteins, bacteria, crystals or other deposits) which are normally present in the urine from adhering. Other synthetic polymers with these physical properties towards biological material are known to the skilled person, including polyurethane or any other material which is bioresistant to incrustation in urine.

The outer layer of this mixed structure, intended to come into contact with surrounding living tissue, has optimum biocompatibility characteristics. For tubular elements 1 and 3, the outer layer is in the form of a strip which is wound in a spiral around the inner layer which has a tubular form, or in the form of a tube extruded directly around the inner layer. The two layers of tubular elements 1 and 3 are integral with each other.

The outer layer is composed of a polymer which can prevent any rejection of the living organs remaining in permanent contact with the implant. Polymers with these characteristics are also known and are, for example, used in cardiovascular prostheses, examples being polytetrafluoroethylene or any other porous biomaterial, such as polyurethane, which enables the surrounding tissue to penetrate, thus ensuring the liquid tightness of the assembly.

The mechanical connection means of the artificial implant of the invention uses turnbuckles, worm drive clips, collars or rings to connect together the different elements which replace the urinary system. These connections are essentially formed with the integral mixed structure described above.

These mechanical connections eliminate the need for the formation of anastomoses to hold the assembly and thus guarantee its liquid tightness. The risk of leaks is thus advantageously eliminated. Further, replacement of one or more of the elements of the implant, in the event of failure thereof, is more simple, as a mechanical connection only has to be disconnected and the failed part removed instead of carrying out a surgical intervention to disconnect an anastomosis.

The implant assembly is retained by the mixed structure constituting the implant, adapted to form means for direct fixing of tubular elements 1 to each renal parenchyma 9. The outer layer 8 has folds 10 located in a spiral or in a ring, these folds advantageously ensuring direct anchorage of the implant on the renal parenchyma. At the distal ends 11 of the ureters, the outer wound layer has been taken back to facilitate their introduction into the renal cavities.

The form and constitution of the elements of the implant are such that they are flat when empty and can pass from this state to an expanded state and vice versa when it fills or is emptied. The thickness of the layers is adapted by the skilled person so that the selected materials, depending on the criteria of the invention as defined above, are sufficiently flexible to pass from a flattened state to an expanded state. The structure is also initially constrained so as to be in its flattened form when empty.

Thus the mixed structure of the artificial implant of the invention enables it to be implanted under the skin via para-iliac incisions using a balloon using a technique which is known to the skilled person.

Reservoir 2 constituting the portion of the implant acting to replace the natural bladder is illustrated in FIG. 2, which is a sectional view along the line II—II of FIG. 1. It is constituted by an outer shell 12 formed from the same biocompatible material as the outer shell described above, and by a flexible inner pouch 13 constituted by the same material as the inner layer described above. The flexible inner pouch is not integral with the outer shell: it remains free inside it, following its form when it is filled. This inner pouch has a maximum capacity of about 500 milliliters.

Protuberances 14 on the inner pouch (one only is visible in the Figure; the other, which is symmetrical, is hidden) which extend beyond the outer shell, act as a connection between reservoir 2 and tubular elements 1 constituting the ureters, via mechanical connections. A further protuberance 14' on the inner pouch constitutes the start of the tubular element constituting the urethra. These protuberances are formed by elongation or by any means known in the art (moulding, adhesion, fusion . . . ) depending on the constituent material used.

The tubular elements constituting the ureters and urethra are also produced with the mixed structure described above.

FIG. 3 shows more detail of the mechanical connection 5 between the vesical reservoir 2 and ureters 1, of a shrink ring type in this embodiment where ureter 1 is push fitted into protuberance 14 of inner pouch 13 of reservoir 2. These mechanical connections, which can be present in other forms, for example worm drive clips, facilitate partial replacement of each of the constituent elements.

In particular, these connections permit easy removal and thus easy replacement of the flexible pouch. Advantageously, the material used for the inner layer and its thickness are selected so that the pouch is sufficiently flexible to be able to fold on itself upon removal. Reconstitution of the vesical reservoir is thus facilitated and can be achieved with a simple surgical intervention, the other elements of the urinary system being left in place.

FIG. 4 shows reservoir 2 and its extensions along a partial side view of FIG. 1, implanted subcutaneously. Reservoir 2 is located between skin P and the pelvic muscle 15. Urethra 3 with its sphincter system 4 passes in front of the pubic bone 16 for insertion into the final natural evacuation channel 17. Ureters 1 are connected to the other end of reservoir 2 via connector 5.

Further, and as shown in FIG. 5, urine stored in the inner pouch of vesical reservoir 2 is emptied by simple manual depression 18 by pressing on the anterior portion 19 of the reservoir, readily accessible under skin P because of its subcutaneous implantation. The reservoir deforms, following dotted lines 2'. Outer shell 12, in particular portion 19 of this shell, is advantageously thicker than the outer layer of the ureters and urethra, so as to increase its strength without substantially reducing its flexibility.

The pressure exerted on reservoir 2 causes artificial sphincter 4 to open, to enable urine to exit through urethra 3. The choice of sphincter is guided by its capacity to be able to closely follow the ejection of urine.

This expulsion of urine accompanied by simultaneous closing of artificial sphincter 4 creates a slight negative pressure inside pouch 12 of reservoir 2. This slight negative pressure, which is maintained after closure of sphincter 4, is sufficient to ensure continuous drainage of fluids from the kidneys to reservoir 2 through the ureters 1.

Advantageously, the negative pressure created by emptying reservoir 2 prevents reflux of urine to the top of the urinary system, eliminating the risk of hydronephrosis or renal insufficiency.

For this reason, the artificial implant of the present invention does not require the positioning of complex devices such as ureterovesical or urethrovesical anti-return valves which are indispensable in current implants intended to completely replace the urinary system. As a result, the artificial implant of the present invention is cheaper and the surgical intervention required to place it in position is simple, non invasive and not very traumatising to the patient.

FIGS. 6a to 6c illustrate different embodiments of the artificial urethral sphincter, constituted by a system enabling compression and decompression of the artificial urethra 3 in front of pubis 16 to enable the vesical reservoir to be emptied.

This compression/decompression of the artificial urethra can be activated, for example, by a manual valve 20 with a spring 21 (FIG. 6a), by an electromagnetic turbine 22 (FIG. 6a) or by introducing a non-return valve 23 (FIG. 6c).

Like the other elements of the implant of the invention, this decompression system is connected to the assembly by non anastomosed mechanical connections which can readily be destroyed to facilitate their partial replacement if needed.

The invention is not limited to the examples described and illustrated. It is, for example, possible to use a variety of forms for the reservoir replacing the bladder, for the artificial ureters and urethra and for the mechanical connections; the spiral form of the outer layer of the tubes can, for example, be replaced by any form. Further, the connections can be made over a length which is adapted to the materials used and to their thickness; the interval between the inner pouch and the shell of the reservoir can also be varied and can be adapted.

What is claimed is:

1. An artificial implant for a urinary system comprising:
a flexible reservoir having an outer shell and an inner pouch, wherein said inner pouch is not attached to said outer shell and is thus extractable;
two input tubular elements opening into the interior of said inner pouch and which are fixed to said reservoir via mechanical connections and which are connectable to two renal parenchymas at the other end;
an outlet tubular element opening into said inner pouch and containing an artificial urethral sphincter;
wherein said reservior, said input tubular elements, and said output tubular element each has an outer layer and an inner layer, wherein said outer layer is a biocompatible material and said inner layer is a material that prevents adhesion of biological residues; and
wherein said reservoir and input and output tubular elements have a flattened state when empty and an expanded state.

2. The artificial implant according to claim 1, wherein the reservoir deforms when manual pressure is applied on the exterior of the skin near said reservoir wherein upon deformation the artificial sphincter opens.

3. The artificial implant according to claim 1, wherein said mechanical connections between the reservoirs and the two input tubular elements are supported by protuberances of the inner pouch.

4. The artificial implant according to claim 1 or claim 3, wherein said mechanical connections are selected from turnbuckles, worm drive clips and rings.

5. The artificial implant according to claim 1, wherein said input tubular elements connectable to each of the renal parenchymas have external spiral folds or external ring folds which attach directly to the renal parenchymas.

6. The artificial implant according to claim 1, wherein a negative pressure is maintained in said reservoir.

7. The artificial implant according to claim 1, wherein said artificial urethral sphincter is activated by a mechanical spring valve.

8. The artificial implant according to claim 1, wherein said artificial urethral sphincter is activated by an electromagnetic valve.

9. The artificial implant according to claim 1, wherein the outer shell is made of a porous biomaterial.

10. The artificial implant according to claim 1, wherein said inner pouch is made of a biomaterial which is resistant to encrustation by urine.

11. The artificial implant according to claim 1, wherein said artificial implant is implanted under the skin via para-iliac incisions using a balloon technique.

* * * * *